United States Patent [19]

Janszen

[11] Patent Number: 5,113,867
[45] Date of Patent: May 19, 1992

[54] FLUID FLOW CHARACTERIZING

[76] Inventor: David A. Janszen, 82 Park St., Apt. 3, Medford, Mass. 02155

[21] Appl. No.: 525,189

[22] Filed: May 16, 1990

[51] Int. Cl.$^5$ .............................................. A61B 8/06
[52] U.S. Cl. .............................. 128/661.09; 73/861.25
[58] Field of Search ...................... 128/661.07–661.10; 73/861.25

[56] References Cited

U.S. PATENT DOCUMENTS

| | | | |
|---|---|---|---|
| 4,640,292 | 2/1987 | Tykulsky | 128/661.09 |
| 4,848,355 | 7/1989 | Nakamura et al. | 128/661.07 |

OTHER PUBLICATIONS

Atherton, J. P., "Phase-Locked Loop", IEEE Proc., vol. 129, Pt. A, No. 6 (Aug. 1982).
Brandestini, Marco, "Topoflow—A Digital Full Range Doppler Velocity Meter", IEEE Trans. Sonics & Uts, vol. SU-25, No. 5, Sep. 1978.
C. J. Hartley et al.—An Ultrasonic Pulsed Doppler System for Measuring Blood Flow in Small Vessels—Journal of Applied Physiology, vol. 37, No. 4, Oct. 1974—pp. 626-629.
Donald W. Baker—Pulsed Ultrasonic Dopper Blood—Flow Sensing—IEEE Transactions on Sonics and Ultrasonics, vol. SU-17, No. 3, Jul. 1970—pp. 170-184.
Y. Takeda—Velocity Profile Measurement by Ultrasound Doppler Shift Method—International Journal of Heat & Fluid Flow, vol. 7, No. 4, Dec. 1986—pp. 313-318.
Remo M. Lutolf et al.—Ultrasonic Phased-Array Scanner with Digital Echo Synthesis for Doppler Echocardiography—IEEE Transactions on Ultrasonics, Ferroelectrics, and Frequency Control, vol. 36, No. 5, Sep. 1989—pp. 494–506.
P. A. Grandchamp—A Novel Pulsed Directional Doppler Velocimeter: The Phase Detection Profilometer—Proceedings of the European Congress on Ultrasound in Medicine, 2nd; Elsevier Publishing Co., New York, N.Y. 1975; pp. 137-143.
P. M. Gammell—Improved Ultrasonic Detection Using the Analytic Signal Magnitude—Ultrasonics, Mar. 1981—pp. 73-76.
F. D. McLeod et al.—A Digital Doppler Velocity Profile Meter—Rocky Mountain Bioengineering Symposium, 11th, paper; Apr. 15-17, 1974—pp. 55-60.
M. I. Skolnik—Introduction to Radar Systems—McGraw-Hill Book Co., Inc., New York, N.Y., 1962; pp. 113-163.
P. A. Peronneau et al.—Doppler Ultrasonic Pulsed Blood Flowmeter—International Conference on Medicine and Biological Engineering, 8th; Jul. 20-25, 1969,; session 10-11—(one page).
D. W. Baker et al.—A Phase Coherent Pulse Doppler System for Cardiovascular Measurements—Annual Conference on Engineering in Medicine and Biology, 20th; Nov. 13-16, 1967; paper 27.2 (one page).

*Primary Examiner*—Francis Jaworski
*Attorney, Agent, or Firm*—Henry D. Pahl, Jr.

[57] ABSTRACT

The apparatus disclosed herein utilizes ultrasound to characterize the flow of fluid material containing suspended particles. Energy scattered by particles in the moving fluid from a brief emitted burst is detected to obtain a return signal and this return signal is compared with a preselected amplitude at a preselected time interval after each burst. Preferably the amplitude threshold is an integrated or filtered value corresponding to the amplitude of the return signal over some earlier time. A binary output signal is generated which continues from each comparison to the next at a level corresponding to the result of the comparison. Accordingly, the output signal includes frequency components representative of Doppler shifts occasioned by the movement of fluid.

5 Claims, 3 Drawing Sheets

FLUID FLOW CHARACTERIZING

BACKGROUND OF THE INVENTION

The present invention relates to fluid flow measurement apparatus and more particularly to such apparatus which employs pulsed Doppler ultrasound.

In order to characterize or measure blood flow in a vessel beneath the patient's skin, it has heretofore been proposed to employ ultrasound and to detect or demodulate Doppler shifted components in that portion of the ultrasound energy which is scattered back from the moving blood. The measurement can be performed either invasively, e.g. by means of a catheter, or non-invasively, e.g. by a transducer placed on the patient's skin adjacent a vessel near the surface. Typically, the demodulation of the back scattered energy has involved mixing, e.g. in an analog multiplier circuit, of the returned signal with a reference signal which is coherent with the originally emitted burst. The resulting signal, which represents the relative phase of the received energy, is low pass filtered to remove carrier residue and sum components and sampled at a substantially fixed time interval following each burst to localize velocity sensing to a fixed region. This region is displaced from the transducer by a distance which is proportional to the time interval. The sampling step is followed by low pass filtering to remove frequency components arising from the sampling process itself and to select out the Doppler shifted components [Hartley, C. J. and Cole, J. S.: *An ultrasonic pulsed Doppler system for measuring blood flow in small vessels*. Journal of Applied Physiology 1974; 37: 626-9] [Baker, D. W.: *Pulsed Doppler blood-flow sensing*. IEEE Transactions on Sonics and Ultrasonics 1970; SU-17, n3: 170-84]. In order to derive an estimate of the frequency components of the Doppler signal, which is a measure of flow velocities, Doppler signals have been processed by both analog and digital means. Analog processing has typically consisted of zero crossing counting to obtain a mean frequency estimate [Hartley and Cole]. In digital processing, the Doppler signal has been digitized using an analog to digital (A/D) converter and subsequently processed using digital signal processing (DSP) methods such as the Fast Fourier Transform (FFT) to obtain detailed spectral information [Takeda, Y.: *Velocity profile measurement by ultrasound Doppler shift method*. International Journal of Heat and Fluid Flow 1986; 7, n4: 313-8] [Lutolf, R. M. et al.: *Ultrasonic phased-array scanner with digital echo synthesis for Doppler echocardiography*. IEEE Transactions on Ultrasonics, Ferroelectrics, and Frequency Control 1989; 36 n5: 494-506].

Accuracy in the characterization of flow conditions benefit from maximization of two principle qualities of pulsed wave Doppler velocity measurement: 1. spatial resolution, to allow interrogation of many small sample volumes within a flow stream simultaneously (multiple channels), and 2. accurate and detailed estimation of the complex spectrum of frequency components present in the Doppler signal (representing blood cell velocities) from each sample volume. Methods involving analog mixing possess inherent limitations on spatial resolution imposed by the finite duration of the time required to sample the demodulated (phasic) signal (>0.2 us), as well as inherent limitations o location certainty imposed by the slew rate and settling time of the S/H circuit which cause errors related to the derivative of the sampled voltage. Also, to obtain the best spectral estimate requires high-speed A/D conversion followed by cumbersome forms of spectrum analysis, e.g. computation-intensive FFT processing. Multi-channel implementations bearing spectral analysis, though possible, become prohibitively complex [Lutolf et al].

Another demodulation method has involved the comparison of the phase of the entire returned signal from one burst to the [next [Grandchamp, P. A.: *Novel pulsed directional Doppler velocimeter: the phase detection profilometer*. Proceedings of the European Congress on Ultrasound in Medicine, 2nd; Elsevier Publishing Co., New York, N.Y. 1975; p 137-43]. By providing a continuous measure of frequency shift (phase change per burst) vs. range, this inherently eliminates the sampling requirement, but has the disadvantage of relying on MTI echo cancellation techniques as discussed in the next paragraph. Other methods have involved directly digitizing the raw received signal using an A/D converter with subsequent DSP to demodulate the Doppler components (Gammel, P. M.: *Improved ultrasonic detection using the analytic signal magnitude*. Ultrasonics 1981; 19, n2: 73-6]. This method requires extremely high speed A/D converters (100 MSPS) with attendant high data rates and speed related design difficulties, and requires specialized, high speed DSP for real-time processing and display, all of which are associated with high cost.

An obstacle to simple acquisition of a pulsed wave Doppler signal is that, because short pulses of ultrasound are transmitted into the tissue, fixed interfaces in the path of the ultrasound beam, e.g. between the blood and the blood vessel, which function as relatively efficient, diffuse reflectors, result in the presence of large, undesired stationary components (fixed echoes) in the received signal. The amplitude of these undesired components is on the order of 40 dB higher than that of the desired Doppler shifted components [McLeod, F. D., et al.; *A digital Doppler Velocity profile meter*. Rocky Mountain Bioengineering Symposium, 11th, paper; Apr. 15-17, 1974; p 55-60].

The principal mean for reducing the relative level of the stationary components has been the Moving Target Indicator (MTI), adapted from radar applications [Skolnik, M. I.: *Introduction to Radar Systems*: McGraw-Hill Book Co., Inc., New York, N.Y. 1962; p 113]. This method relies on the use of highly stable, wide bandwidth delay lines which are bulky, expensive, require calibration, and carry the need for complex adjunctive circuitry requiring periodic adjustments. This renders MTI techniques impractical for medical applications of the sort contemplated. Filter [Hartley and Cole] [Peroneau, P. A. and Leger, F.: *Doppler ultrasonic pulsed Doppler blood flowmeter*. International Conference on Medicine and Biological Engineering, 8th; Jul. 20-25, 1969; session 10-11] and sample/hold (S/H) [Baker, D. W. and Watkins, D. W.: *A phase coherent pulse Doppler system for cardiovascular measurements*. Annual Conference on Engineering in Medicine and Biology, 20th; Nov. 13-16, 1967; paper 27.2] techniques of stationary echo suppression have also been used. The filtering implementations have had the reputed disadvantage of laborious design and assembly, and certainly limit the response to low velocities. S/H circuitry imposes the limitation mentioned earlier on spatial resolution and location certainty and one S/H is required for each channel in a multi-channel system.

Among the several objects of the present invention may be noted the provision of novel apparatus for characterizing the flow or movement of any fluid material containing suspended solid, liquid or gaseous particles; the provision of such apparatus which can be employed remotely in that the sensing element is not necessarily brought into contact with the fluid under interrogation and does not therefore disturb the movement of that fluid; the provision of such apparatus which generates a signal including frequency components representative of Doppler shifts occasioned by the movement of the fluid; the provision of such apparatus which is highly accurate and reliable; the provision of such apparatus which yields reproducible results; the provision of such apparatus which is of relatively simple and inexpensive construction; the provision of such apparatus which may be relatively simple and inexpensive to expand into a multi-channel implementation. Other objects and features will be in part apparent and in part pointed out hereinafter.

SUMMARY OF THE INVENTION

The apparatus of the present invention is intended to characterize the flow of fluid containing suspended particles at some selectable distance from a transducer. The transducer is repetitively energized electrically to emit ultrasonic bursts. The transducer may function as a receiver of scattered ultrasound, and one or more receive-only transducers may also be present. One or more receiver circuits provide a return signal corresponding to acoustic energy received by one or more transducers. The amplitude of each return signal is compared with a preselected amplitude threshold at a preselected time interval after each burst, which interval corresponds to the selected distance. A digital output signal is generated which continues from each comparison to the next at a level corresponding to the result of the comparison. Accordingly, the output signal includes frequency components representative of Doppler shifts occasioned by the movement of fluid relative to the transmitting transducer. Preferably, the amplitude threshold is an integrated or stored value corresponding to the return signal over some earlier time.

DESCRIPTION OF THE PREFERRED EMBODIMENT

Figure 1:
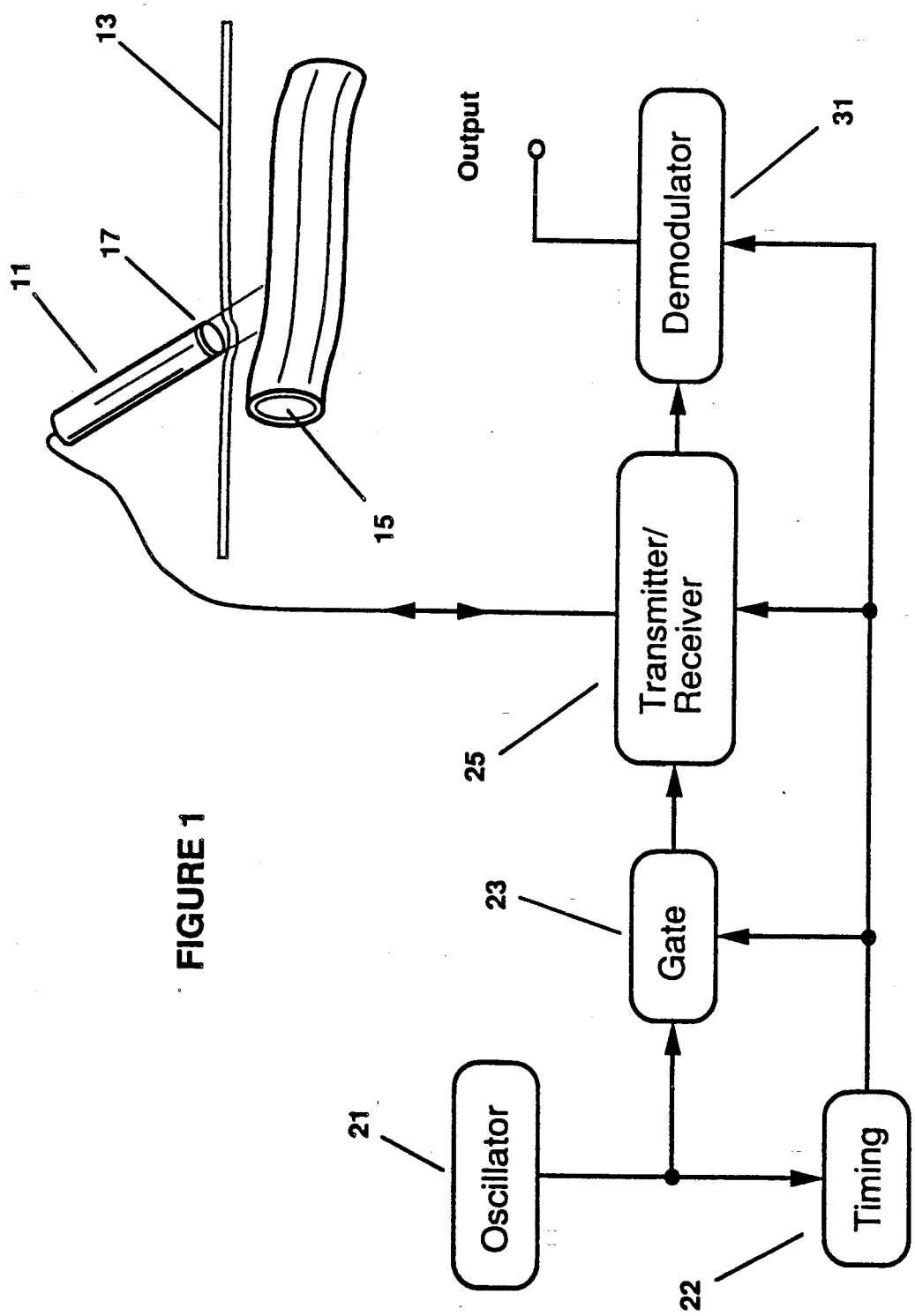
FIG. 1 is a block diagram of Doppler ultrasound apparatus in accordance with the present invention.

Referring now to FIG. 1, there is indicated by reference character 11 a transducer assembly generally, which is adapted to be pressed against the skin of a patient over a selected blood vessel, e.g., the radial artery which extends essentially parallel to the skin a small distance below the surface. In FIG. 1, the patient's skin is indicated by reference character 13 and the artery by reference character 15. Within the transducer assembly 11, an ultrasonic transducer crystal 17 is oriented so as to emit ultrasonic energy at an angle to the skin, e.g., 45 degrees. The ultrasonic energy is coupled to the skin through a suitable coupling medium. Movement of blood in the vessel 15 will result in Doppler shifted components in energy backscattered from the blood when the transducer is energized.

An oscillator 21 provides a signal at suitable ultrasonic frequency, e.g., 20 megahertz. This high frequency signal is counted down by timing sequencer circuitry, as indicated at reference character 22. Gating circuitry 23 is controlled by the sequencer 22 to repetitively gate the high frequency signal so as to generate appropriate short bursts of the ultrasound frequency which are applied to a transmit/receive (T/R) switching circuit 25 which causes the pulses to be applied to the transducer crystal 17. The T/R circuitry is described in greater detail hereinafter.

Backscattered ultrasonic energy picked up by the transducer crystal 17 is coupled back through the T/R switch 25 to a demodulator circuit 31 which is operated to detect zero crossings as described hereinafter.

Figure 2:
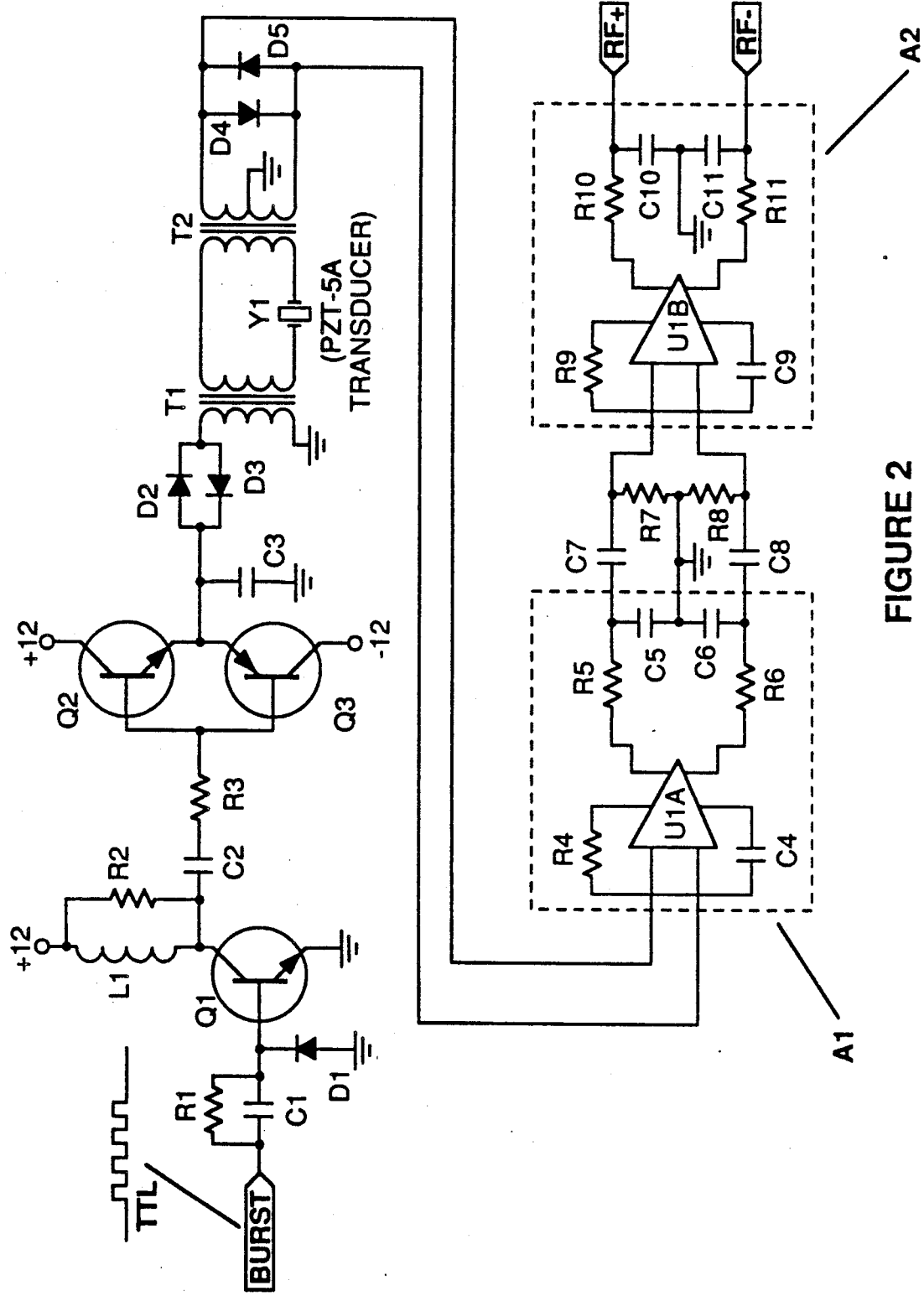
FIG. 2 is a schematic circuit diagram illustrating transmit/receive circuitry employed within the apparatus of FIG. 1.

FIG. 2 illustrates the T/R switch circuitry in detail though in the following description only genera functional characteristics are described since many possible variations in the details will be apparent to those skilled in the electronics art. The gated burst signal obtained from the gating circuitry 23 is level shifted in a first stage amplifier employing transistor Q1 and is a.c. coupled, through a pair of complementary emitter-follower transistors Q2 and Q3 and a pair of back-to-back diodes D2 and D3, to the primary winding of the first of a pair of transformers T1 and T2. The amplitude of the driving signal is sufficient to forward bias the diodes D2 and D3 into conduction so that energy is transmitted through transformer T1. As is understood, the diodes exhibit an essentially predetermined voltage threshold before conducting.

The secondary winding of transformer T1 is coupled to the probe transducer and to the primary winding of the second transformer T2, connected in series. The balanced secondary winding of the transformer T2 is connected to a pair of back-to-back diodes D4 and D5 which are connected so as to clip the output voltage. The transmitted signal is of sufficient amplitude to forward bias these diodes so that, when they are conducting, the secondary of transformer T2 appears to be shorted and thus most of the energy is coupled to the probe transducer. Again, these diodes exhibit an essentially predetermined voltage threshold before conducting.

A received signal is coupled over to the secondary winding of transformer T2. The amplitude of the received signal is, however, substantially lower than the amplitude of the transmitted signal and thus the shunt diodes D4 and D5 do not become forward-biased and the received signal is coupled to the first of two stages of bandpass tailored amplification A1 and A2. Complementary output signals are generated as indicated at RF− and RF+.

Figure 3:
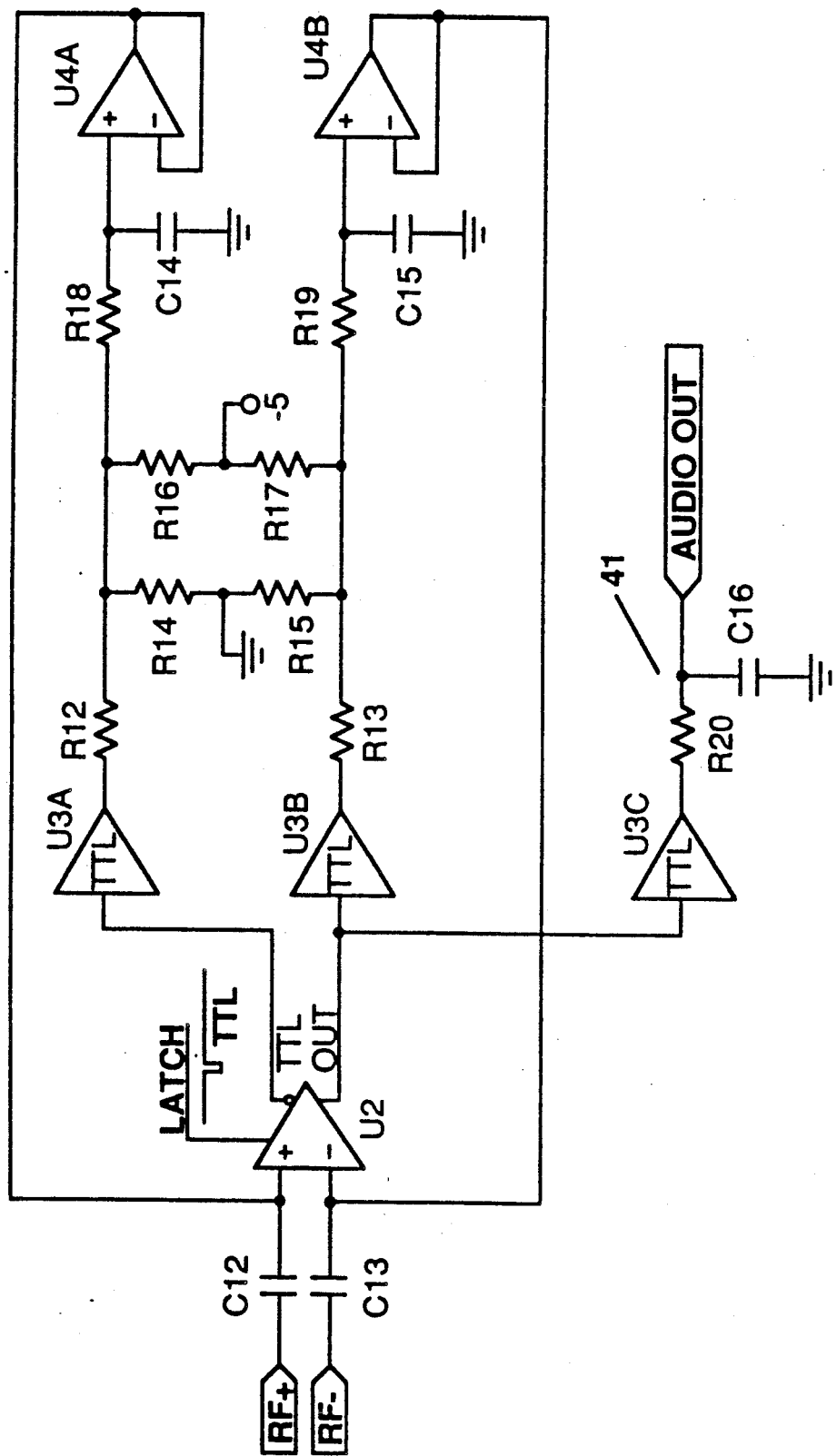
FIG. 3 is a schematic circuit diagram of demodulation circuitry employed in the apparatus of FIG. 1.

The balanced RF signals are applied to the demodulator circuitry 31 which is illustrated in detail in FIG. 3. The demodulator circuitry of FIG. 3 employs a latched comparator, designated by reference character U2, to detect the relative amplitude of the detected RF signal at a particular instant in time relative to the transmitted pulse. The outputs of comparator U2 are buffered by buffers designated U3A through U3C. The delay interval between the transmitted pulse and the latching corresponds to the distance from the transducer to the region where flow is to be detected. Since the timing of the interval is derived by counting down from the high frequency oscillator 21 in the timing sequencer 22, the time of latching is synchronized with the phasing of the oscillator 21.

In one sense, the comparator operates to detect zero crossings in the returned signal. However, at the very low amplitudes encountered in detecting back scattered ultrasound, it is difficult to establish a precise and well-compensated zero level threshold. Thus, in accordance with one aspect of the present invention, a reference threshold is obtained for each comparison based on an integrated or stored value corresponding to the amplitude of the return signal over some earlier time. For this purpose, the inverted binary output from the comparator U2 is low pass filtered or integrated and applied to the non-inverting input of an operational amplifier U4A. Operational amplifier U4A is connected as a follower to buffer the filtered signal for summing with the RF+ signal at the non-inverting input to the comparator U2. R18 and C14 form a simple RC network and define a corner frequency of the 16 Hz for the low-pass input to operational amplifier U4A. The resistor network consisting of resistors R12, R14 and R16 serve both to scale the signal so as to define a loop gain of approximately −3 dB in the passband, and to offset the signal voltage downward by an amount approximating the average of the typical high and low TTL levels of 0.4 volts and 3.5 volts in order to provide a signal with a nominal value of approximately zero volts. A similar circuit incorporating resistors R13, R15, R17, R19, capacitor C15, and operational amplifier U4B provides similar feedback to the inverting input of the comparator U2 based on the non-inverted output of comparator U2, where the signal is filtered using a lower corner frequency of 0.16 Hz. In the embodiment illustrated, the feedback serves to suppress echoes from stationary and slow moving interfaces.

In one sense, the comparator U2 functions as a single bit analog to digital converter. It changes state whenever the first difference of the echo-suppressed, returned signal changes sign at successive comparator strobing times. Each state change corresponds to a 180 degree rotation of the relative phase angle of the returned signal. By utilizing appropriate timing of the strobing of the comparator and, further, by utilizing a floating threshold level as described previously, it has been found that an output signal is obtained which includes the desired Doppler shifted components. By strobing a second such demodulation circuit in coherent quadrature to the originally emitted burst, it has also been found that a second Doppler signal may be obtained in quadrature to the first from which the direction of the phasor rotation may be determined, corresponding to the direction of flow in the region being interrogated.

A buffered output from the comparator is passed through a low pass filter to supply an audio signal as indicated at reference character 41 for direct listening or further processing, e.g., zero crossing counting or FFT. By generating multiple quadrature signals corresponding to multiple strob times between each transmitted burst of ultrasound, it is possible to extract considerable detail regarding the characteristics of flow within the ultrasound beam, e.g. one component of direction, speed, gradients, and turbulence. The information may be further enhanced by using multiple transducers to aid in determining the velocity vectors completely through triangulation.

Existing ultrasonic flow instrumentation has been found to have useful applications in the study of blood flow, in fluid mechanics research, and in industrial flow sensing and control. The present invention offers an increase in spatial resolution, sensitivity, and simplicity over the existing approaches to Doppler flow instrumentation.

As will understood by those skilled in the art, the particular components and circuit values employed in a particular implementation of the present invention will depend upon many factors including the type of vessel to be investigated, the nature of the nature of the transducer used, and so forth. However, a set of component types and values employed in one illustrative embodiment of the present invention are listed in Tables 1 and 2.

TABLE 1

| Item | Quantity | Reference | Part |
|---|---|---|---|
| 1 | 2 | C1,C3 | 100 pF |
| 2 | 1 | C2 | 220 pF |
| 3 | 1 | C4 | 68 pF |
| 4 | 4 | C5,C6,C10,C11 | 33 pF |
| 5 | 2 | C7,C8 | .1 uF |
| 6 | 1 | C9 | 68 pF |
| 7 | 5 | D1,D2,D3,D4,D5 | 1N914 |
| 8 | 1 | L1 | 1 uH |
| 9 | 1 | Q1 | 2N3904 |
| 10 | 1 | Q2 | MPS8099 |
| 11 | 1 | Q3 | MPS8599 |
| 12 | 1 | R1 | 1 k |
| 13 | 5 | R2,R5,R6,R10,R11 | 221 |
| 14 | 3 | R3,R4,R9 | 100 |
| 15 | 2 | R7,R8 | 499 |
| 16 | 2 | T1,T2 | K-type core |
| 17 | 1 | U1 | NE5592 |
| 18 | 1 | Y1 | PZT-5A |

TABLE 2

| Item | Quantity | Reference | Part |
|---|---|---|---|
| 1 | 3 | C12,C13,C14 | .1 uF |
| 2 | 1 | C15 | 10 uF |
| 3 | 1 | C16 | 4700 pF |
| 4 | 2 | R12,R13 | 1 k |
| 5 | 2 | R14,R15 | 1.5 k |
| 6 | 3 | R16,R17,R20 | 3.32 k |
| 7 | 2 | R18,R19 | 100 k |
| 8 | 1 | U2 | AD9698 |
| 9 | 1 | U3 | 74ALS34 |
| 10 | 1 | U4 | LM324 |

In view of the foregoing it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Apparatus for characterizing the flow of fluid bearing suspended particles, said apparatus comprising:
   a transducer;
   driver means for repetitively energizing said transducer to emit an ultrasonic burst;
   means for providing a return signal directly corresponding to acoustic energy received by said transducer without demodulation;
   means for comparing the amplitude of said return signal with a preselected amplitude threshold at a preselected time interval after each burst which interval corresponds to the distance from said transducer to the sample of fluid flow which is to be characterized;

means for providing a binary output signal which is the result of each comparison and which continues from each comparison to the next at a level corresponding to the result of the comparison, whereby said output signal includes frequency components representative of Doppler shifts occasioned by the movement of blood in said vessel.

2. Apparatus as set forth in claim 1 wherein said amplitude threshold is a value corresponding to the amplitude of said return signal filtered over some preceding time.

3. Apparatus as set forth in claim 1 further comprising:

first and second transformers each having a first winding and a second winding;

a first pair of diodes oppositely poled and connected in parallel, said diodes exhibiting an essentially predetermined threshold voltage before conduction;

a second pair of diodes oppositely poled and shunting the secondary winding of said second transformer, said diodes exhibiting an essentially predetermined threshold voltage before conduction;

means connecting the second winding of said first transformer, the first winding of said second transformer and said transducer in series;

means for applying said bursts to the first winding of said first transformer through said first pair of diodes at an amplitude sufficient to forward bias both said pairs of diodes and thereby apply substantial energy to said transducer; and means coupling the second winding of said second transformer to said comparing means whereby backscattered signals received by said transducer at a level insufficient to forward bias said diodes are coupled to said comparing means.

4. Apparatus for characterizing the flow of fluid bearing suspended particles, said apparatus comprising:

a transducer;

driver means for repetitively energizing said transducer to emit an ultrasonic burst;

signal separating means for providing a signal corresponding directly to acoustic energy received by said transducer without demodulation;

a strobed comparator having first and second inputs and being operative, when strobed, to provide a binary output signal corresponding to the relative amplitudes of the inputs;

means for applying said received signal to at least one of said inputs;

means for strobing said comparator a predetermined time interval after each burst;

means for integrating said output signal over a preselected time constant and feeding back the integrated signal to at least one of said inputs thereby to provide a floating threshold against which the amplitude of the received signal is compared, whereby said comparator provides a binary output signal which continues from each comparison to the next at a level corresponding to the result of the comparison, whereby said output signal includes frequency components representative of Doppler shifts occasioned by the movement of blood in said vessel.

5. Signal-separating apparatus for coupling a transducer to a transmit signal generator and to a receiver, said apparatus comprising:

first and second transformers each having a first winding and a second winding;

a first pair of diodes oppositely poled and connected in parallel, said diodes exhibiting an essentially predetermined threshold voltage before conduction;

a second pair of diodes oppositely poled and shunting the secondary winding of said second transformer, said diodes exhibiting an essentially predetermined threshold voltage before conduction;

means connecting the second winding of said first transformer, the first winding of said second transformer and the transducer in series;

means for applying signals provided by said generator to the first winding of said first transformer through said first pair of diodes at an amplitude sufficient to forward bias both said pairs of diodes and thereby apply substantial energy to said transducer; and means coupling the second winding of said second transformer to said receiver whereby backscattered signals received by said transducer at a level insufficient to forward bias said diodes are coupled to said receiver.

* * * * *